United States Patent
Makki et al.

(10) Patent No.: US 8,800,356 B2
(45) Date of Patent: Aug. 12, 2014

(54) ENGINE CATALYST DIAGNOSTICS

(75) Inventors: Imad Hassan Makki, Dearborn Heights, MI (US); James Michael Kerns, Trenton, MI (US); Michael James Uhrich, West Bloomfield, MI (US); Stephen B. Smith, Livonia, MI (US); Pankaj Kumar, Houston, TX (US); Adam Banker, Plymouth, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 462 days.

(21) Appl. No.: 13/247,640

(22) Filed: Sep. 28, 2011

(65) Prior Publication Data
US 2013/0078725 A1    Mar. 28, 2013

(51) Int. Cl.
*G01M 15/10*    (2006.01)
(52) U.S. Cl.
USPC ....................................... 73/114.75
(58) Field of Classification Search
USPC ............................. 73/114.69, 114.71, 114.75
See application file for complete search history.

(56) References Cited

U.S. PATENT DOCUMENTS

| | | | |
|---|---|---|---|
| 6,532,734 B1* | 3/2003 | Nader et al. | 60/277 |
| 6,581,371 B1* | 6/2003 | Orzel et al. | 60/277 |
| 7,440,823 B2 | 10/2008 | Yamamura et al. | |
| 7,440,839 B2 | 10/2008 | Cesario et al. | |
| 7,899,652 B2* | 3/2011 | Lu et al. | 703/2 |
| 8,688,309 B2* | 4/2014 | Baughman et al. | 701/29.1 |
| 2009/0063115 A1* | 3/2009 | Lu et al. | 703/8 |
| 2013/0151063 A1* | 6/2013 | Baughman et al. | 701/29.1 |
| 2013/0180509 A1* | 7/2013 | Makki et al. | 123/672 |

* cited by examiner

*Primary Examiner* — Eric S McCall
(74) *Attorney, Agent, or Firm* — Julia Voutyras; Alleman Hall McCoy Russell & Tuttle LLP

(57) ABSTRACT

Embodiments for predicting catalyst function are disclosed. One example embodiment includes applying a set of parameter readings for a given sample to a support vector machine to generate a classification output, recording a plurality of classification outputs for a plurality of successive samples over a first duration, and indicating catalyst degradation if a threshold percentage of the classification outputs indicates degraded catalyst performance. In this way, catalyst degradation may be indicated using a simplified model that does not require extensive calibration.

20 Claims, 4 Drawing Sheets

ENGINE CATALYST DIAGNOSTICS

FIELD

The present disclosure relates to monitoring a catalyst in a vehicle system.

BACKGROUND AND SUMMARY

Engine catalyst diagnostics may be used to determine whether a catalyst is sufficiently functioning to reduce exhaust gas emissions. Various approaches may be used to identify the catalyst system performance, such as model based approaches, fuzzy logic, etc.

In the various approaches that have been used, there has often been a tradeoff in terms of the amount of "training" data needed, calibration required, and the level of diagnostic accuracy required (e.g., false positive, undetected degradation, etc.). Furthermore, these techniques have often required extensive windowing functions, where data from only selected operating conditions are considered, such as certain speed/load points, steady state operation, etc.

The inventors herein have recognized the issues with the above approach and provide a method to at least partly address them. One example embodiment includes a method of monitoring catalyst performance. The method comprises applying a set of parameter readings for a given sample to a support vector machine to generate a classification output, recording a plurality of classification outputs for a plurality of successive samples over a first duration, and indicating catalyst degradation if a threshold percentage of the classification outputs indicates degraded catalyst performance.

Support vector machines applied to catalyst diagnostics provides the unexpected benefit of simplified calibration, high accuracy, and modest training requirements. Also, as most of the computation is involved in model training, which is an offline process, it is possible to obtain improved real-time implementation with reduced computational requirements.

In one example, the support vector machine classifies a data set by building a hyper-plane that separates the data into two separate classes. The optimal hyper-plane is selected in such a way as to maximize the margin (the distance between the points in either class to the hyper-plane). Further, the support vector machine approach using a linear classification can be extended to non-linear systems by first transforming the original feature space into a higher dimension where the data can be linearly classified, and then building a linearly separable hyper-plane in the transformed dimension. Through the appropriate selection of a transformation function, the proposed approach enables an improved catalyst diagnostic approach to identify degraded catalyst operation with non-intrusive monitoring and simplified calibration, and with significantly reduced windowing. It may be noted, as the classification is carried out for each instance of time, the proposed approach can provide faster data analysis that those in which data is first windowed, before it is analyzed.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
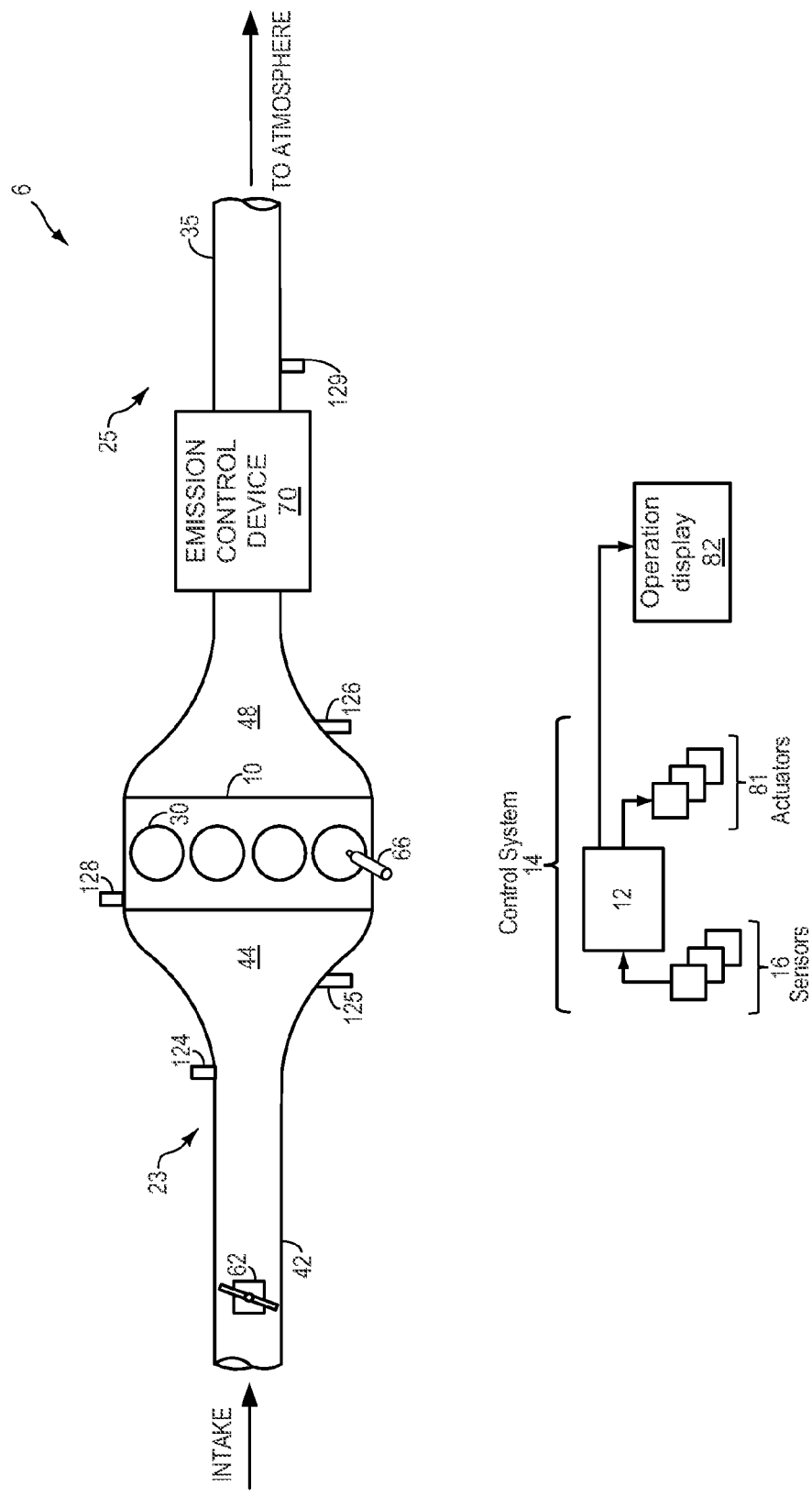
FIG. 1 schematically shows an example vehicle system.
Figure 2:
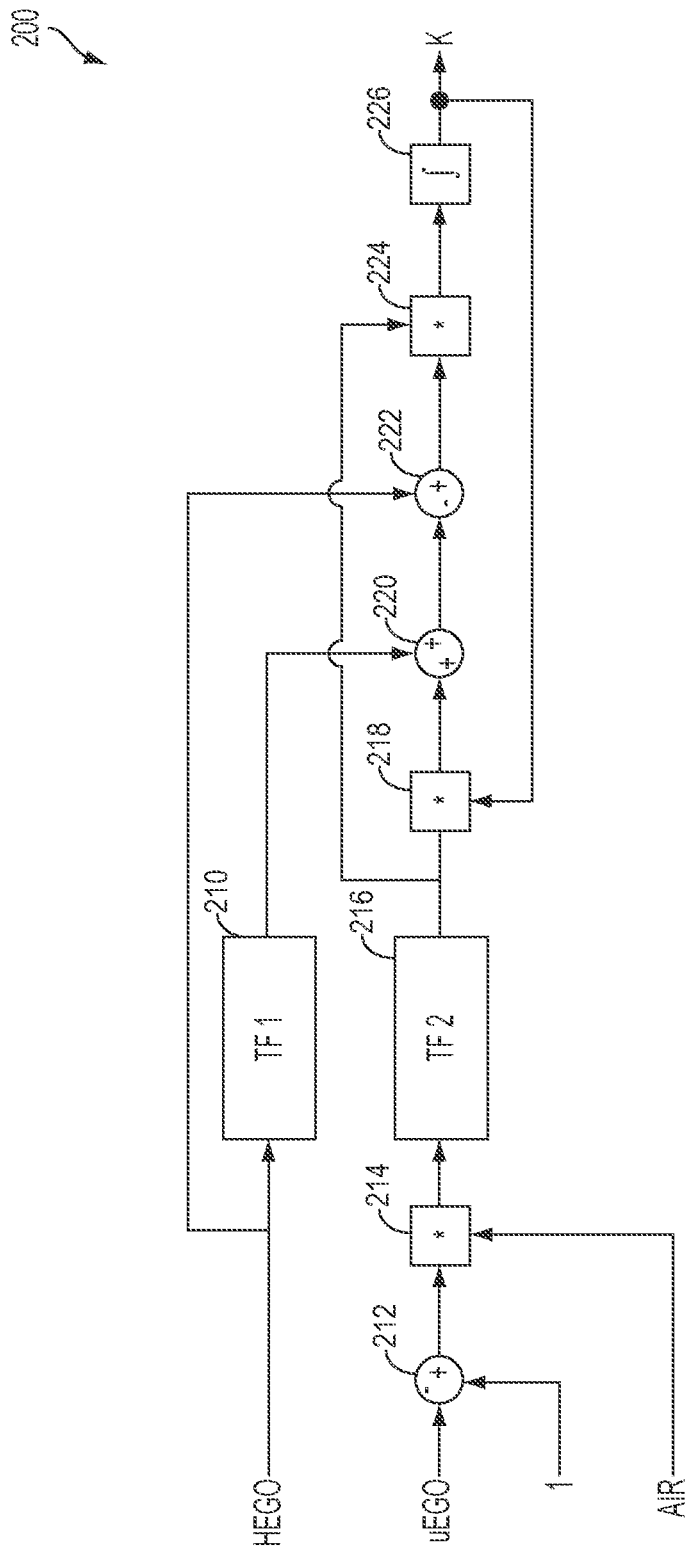
FIG. 2 illustrates a control operation for estimating catalyst gain.
Figure 3:
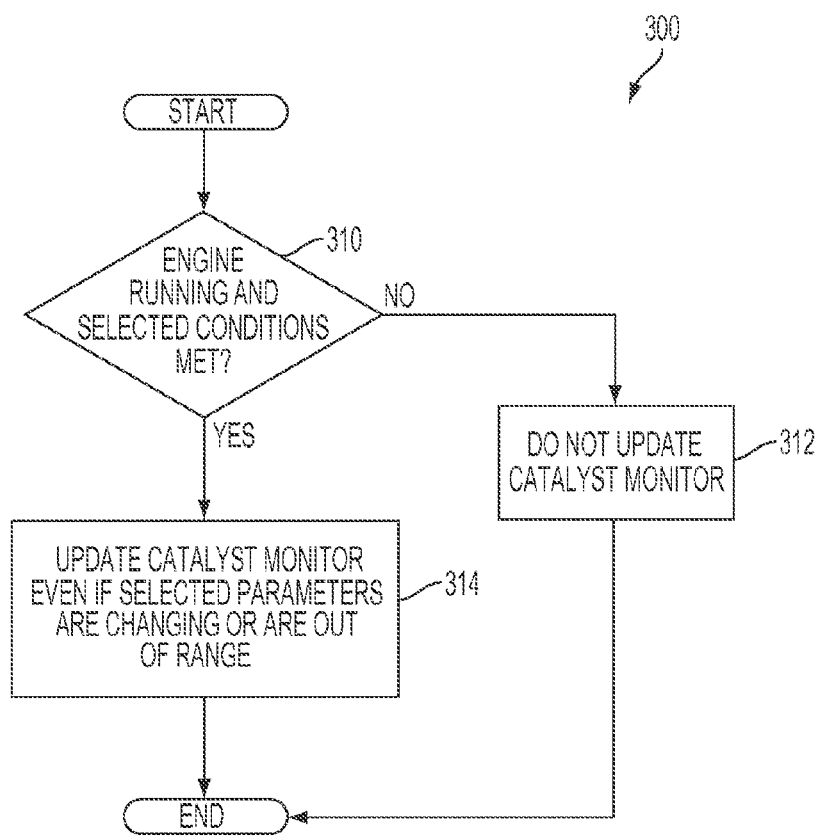
FIG. 3 is a flow chart illustrating an example routine for operating a catalyst monitor.
Figure 4:
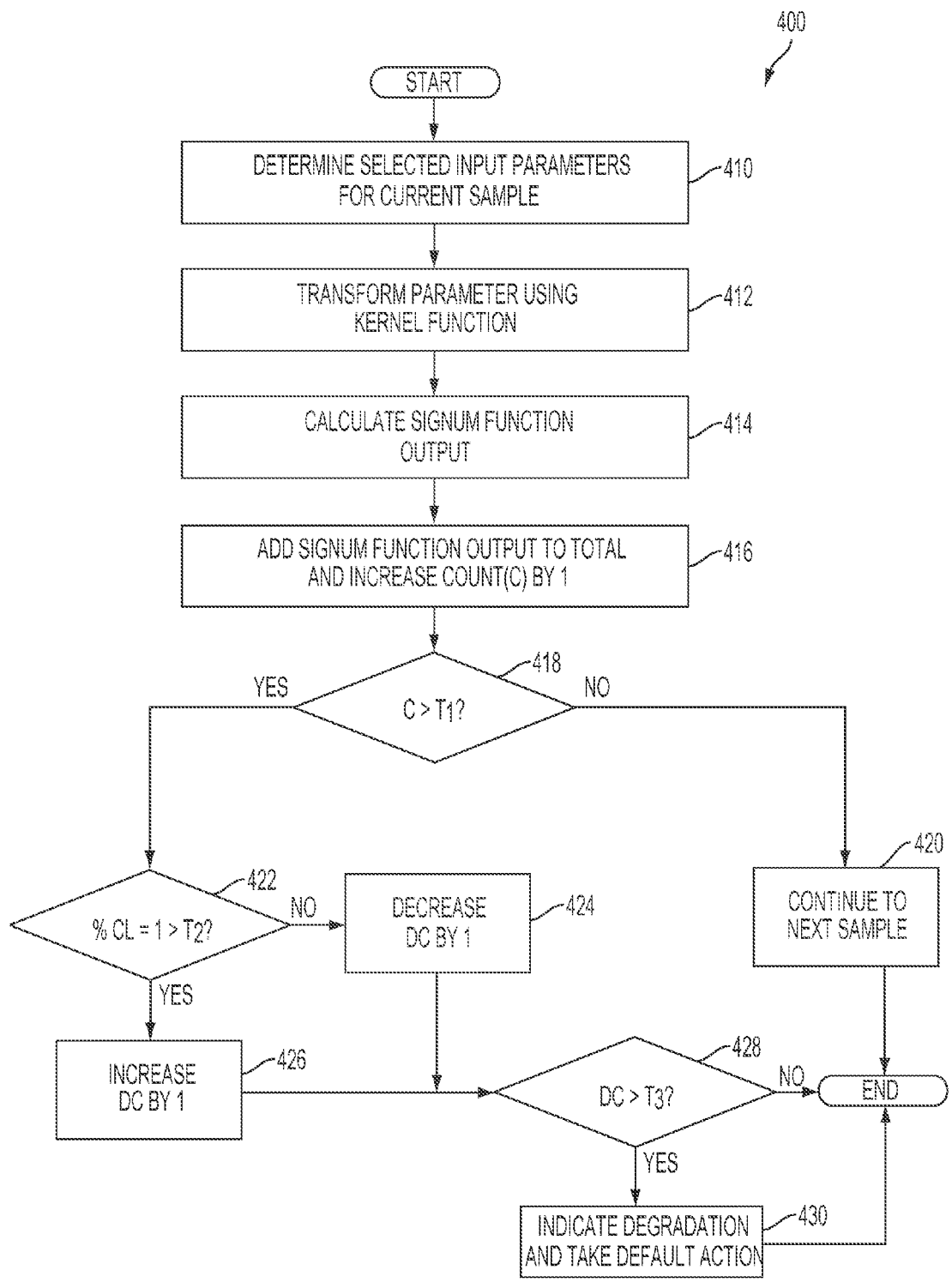
FIG. 4 is a flow chart illustrating an example routine for updating a catalyst monitor.

A support vector machine (SVM) may be used by a catalyst monitor to predict catalyst function. The SVM may be trained using pre-classified, known input parameters. During operation of a vehicle under selected conditions, various unclassified input parameters may be fed into the trained SVM model, and after a pre-defined number of samples have been classified, the total of each classification may be compared to a threshold to determine whether or not the catalyst is functioning. As example vehicle system including a catalyst is depicted in FIG. 1. Example control routines for determining an input parameter and operating the catalyst monitor are shown in FIGS. 2-4.

FIG. 1 shows a schematic depiction of a vehicle system 6. The vehicle system 6 includes an engine 10 having a plurality of cylinders 30. The engine 10 includes an intake 23 and an exhaust 25. The intake 23 includes a throttle 62 fluidly coupled to the engine intake manifold 44 via an intake passage 42. The exhaust 25 includes an exhaust manifold 48 leading to an exhaust passage 35 that routes exhaust gas to the atmosphere. The exhaust 25 may include one or more emission control devices 70, which may be mounted in a close-coupled position in the exhaust. One or more emission control devices may include a three-way catalyst, lean NOx trap, diesel particulate filter, oxidation catalyst, etc. It can be appreciated that other components may be included in the engine such as a variety of valves and sensors.

Engine 10 may receive fuel from a fuel system (not shown) including a fuel tank and one or more pumps for pressurizing fuel delivered to the injectors 66 of engine 10. While only a single injector 66 is shown, additional injectors are provided for each cylinder. It can be appreciated that the fuel system may be a returnless fuel system, a return fuel system, or various other types of fuel system. The fuel tank may hold a plurality of fuel blends, including fuel with a range of alcohol concentrations, such as various gasoline-ethanol blends, including E10, E85, gasoline, etc., and combinations thereof.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust gas sensor 126 (such as a linear UEGO sensor) located upstream of the emission control device, temperature sensor 128, and downstream exhaust gas sensor 129 (such as a binary HEGO sensor). Other sensors such as intake manifold pressure sensor 125, temperature, and composition sensors may be coupled to various locations in the vehicle system 6, as discussed in more detail herein. In one example, an actuator may include a "message center" including an operation display 82 where, in response to an indication of catalyst degradation, a message may be output to a vehicle operator indicating a need to service the emission system, for example. As another example, the actuators may include fuel injector 66, and throttle 62. The control system 14 may include a controller 12. The controller may receive input data from the various sensors, process the input data, and trigger the actuators in response to the processed input data based on instruction or code programmed therein corresponding to one or more routines. Example control routines are described herein with regard to FIGS. 2-4.

The Support Vector Machines (SVM) is a supervised learning algorithm, where given a training set with known class information, a model is developed to classify the unknown test samples into different classes. The SVM processes a set of input data and predicts, for each given input, which of two possible classes the input is a member of, which makes the SVM a non-probabilistic binary linear classifier. In one embodiment, the SVM predicts whether or not the exhaust catalyst is properly functioning. The SVM algorithm may be generated via a set of training examples, each marked as belonging to one of two categories. The SVM training algorithm builds a model that assigns new examples into one category or the other. An SVM model is a representation of the examples as points in space, mapped so that the examples of the separate categories are divided by a clear gap (sometimes referred to as a margin) that is as wide as possible. New examples are then mapped into that same space and predicted to belong to a category based on which side of the gap they fall on.

SVMs use a signum function as a linear classifier to classify the unknown inputs into the two groups based on the training function wherein known inputs are used. Specifically, the known inputs are mapped onto high- or infinite-dimensional space and one or more hyper-planes are chosen that separate the inputs into the two spaced groups. In some embodiments, a hyper-plane that represents the largest margin of separation of the groups is chosen, while in other embodiments, a hyper-plane with a margin that allows for some degree of error in the inputs may be chosen, known as a slack margin. After the model is trained, unknown inputs can be entered and classified into one of the two groups. Typically, the output of the signum function is either +1 or −1, but either classification may be transformed into other values, e.g., −1 may be transformed to 0.

If the known inputs used to train the model cannot be separated using a linear classification, a transformation function may be used with a non-linear classification to separate the inputs. In one embodiment, the present application includes a non-linear classification approach utilizing a kernel function in the SVM for application of the input parameters to predict catalyst performance, along with a soft margin to introduce some slack variables to the classification to allow some misclassification for outlier data points.

For catalyst diagnostics, various input parameters into the SVM may be used. In one embodiment, the input parameters may include catalyst gain, air amount (AM) such as mass airflow rate from MAF sensor 124, catalyst temperature estimated based on engine operating conditions such as speed, load, etc., HEGO output, and UEGO output. In some embodiments, all the example inputs listed above may be used in the SVM. In other embodiments, only a subset of the input parameters may be used, such as catalyst temperature and catalyst gain.

The catalyst gain is an on-line estimation of the oxygen storage capacity in the catalyst, and is illustrated in FIG. 2. The example function of FIG. 2 shows that the catalyst gain is a function of airmass, catalyst temperature, and relative exhaust air-fuel ratio (e.g., lambda). The catalyst gain can be indicative of catalyst conditions, such as an amount of oxygen stored in the catalyst, catalyst conversion efficiency, etc.

FIG. 2 illustrates an example function 200 of calculating catalyst gain from UEGO and HEGO sensor inputs. The catalyst gain may be defined as a linear, time-independent system that responds as an impulse to the inputs described above. Determining the catalyst gain relies on transfer functions (TF), which represent the relationship between the inputs and the outputs in the system. The two transfer functions (TF) are shown below in the laplace domain with s being the Laplace operator:

$$\frac{a}{s+a} \qquad \text{Transfer function 1 (TF1)}$$

$$\frac{b(s)}{conv([x\ y],[x\ z])(s)} \qquad \text{Transfer function 2 (TF2)}$$

Where w=conv(u,v) convolves vectors u and v. Algebraically, convolution is the same operation as multiplying the polynomials whose coefficients are the elements of u and v.

Determining the catalyst gain comprises determining the output of TF1 using input from the HEGO sensor at 210. This output may fed into the output of TF2, as will be described in more detail below. At 212, the difference between the UEGO sensor output and lambda (e.g. 1) is determined, and this difference is multiplied by the air mass at 214. This product is used as the input for TF2 at 216. As the catalyst gain may be calculated and updated continually the output of previous catalyst gain determinations may be fed into the function at 218. The product of TF2 and previous catalyst gain may be added to the output of TF1 at 220. At 222, the difference is determined between the input from the HEGO sensor and the product of 220, and this is multiplied by the output of TF2 at 224. To determine the catalyst gain, K, the integral is taken at 226 of the product determined in 224.

FIGS. 3 and 4 are flow charts illustrating routines that may be executed by controller 12 in order to monitor catalyst function. FIG. 3 shows an example routine for determining when to operate a catalyst monitor using the SVM model to determine catalyst function. If it is determined the catalyst monitor is to be updated, an SVM algorithm may be used applying the above identified inputs (e.g., catalyst temperature, air mass, and gain) to generate a classification for a given set of inputs. In this example, the inputs are each selected from the same sample instance (e.g., sample time) and provided to the SVM algorithm to generate a classification output. As will be described in more detail below, a plurality of classifications are generated for a plurality of respective sample instances over a duration of engine operation following the engine start (see FIG. 4). Once a classification is generated over the entire duration, a percentage of acceptable performance classifications out of the total number of classifications made during the duration is compared to a threshold to determine whether the catalyst is functioning sufficiently. If not, the process is repeated for a plurality of durations until repeatable results are obtained for identifying the catalyst functionality.

Turning to FIG. 3, routine 300 comprises determining at 310 if the engine is running and if selected conditions are met. The selected conditions may include that the input parameters are operational, for example, that the UEGO and HEGO sensors are at a temperature whereby they are outputting functional readings. Further, the selected conditions may include that combustion is occurring in the cylinders of the engine, e.g. that the engine is not in a shut-down mode such as deceleration fuel shut-off (DFSO).

If it is determined that the engine is not running and/or the selected conditions are not met, routine 300 proceeds to 312 and does not update the catalyst monitor. If the engine is running and the selected conditions are met, routine 300 updates the catalyst monitor at 314. The catalyst monitor may be updated even if selected input parameters are changing or out of range.

FIG. 4 illustrates a routine 400 for updating the catalyst monitor. Routine 400 comprises determining selected input parameters for a current sample at 410. Input parameters may be catalyst temperature, catalyst gain, oxygen sensor output, etc. At 412, the selected input parameters are transformed using a kernel function. As explained above, non-linear inputs may be transformed using the kernel function. Various kernel functions may be used, such as a linear, polynomial, radial basis function, sigmoid, and others. In one example, the radial basis function may be used:

$$K(x_i, x_j) = \exp(-\gamma \|x_i - x_j\|^2)$$

In one embodiment, $\gamma=100$, and the soft basis parameter $C=1000$, where $x_i$, $x_j$, ... etc. are the input parameters.

At 414, the signum function output is calculated. The signum function determines a sign, or classification, for the output of the SVM. The SMV may be trained based on known inputs, and may include a set of model parameters that are used to predict an output from unclassified input parameters. Each input parameter determined at a single instance of time may be fed into the SVM model, and a signum function output produced based on:

$$y_i = +1 \text{ if } (\langle w, x_i \rangle + b) \geq 1$$

$$y_i = -1 \text{ if } (\langle w, x_i \rangle + b) \leq 1$$

With a hyper-plane of $(w, x_i) + b = 0$, and where $y_i$ is the predicted class for the test input $x_i$. $w$ is defined by the trained SVM model based on the support vectors computed from optimizing the margin of the hyper-plane.

In one embodiment, to reduce the number of support vectors or to reduce the data size of the trained model for implementation in a vehicle, clustering can be used. Clustering includes an un-supervised learning where the data set is divided into different clusters or groups, so as to minimize the total distance of each point from the respective centroid. In a simpler language, the datapoints which are closer to each other are assigned to one cluster. This technique is employed to initially divide the training set into K (pre-defined number) clusters in each class and then the SVM algorithm is used where the original dataset is replaced by the centroid of each clusters. It was observed that the significant reduction in the number of support vectors could be achieved without loss in accuracy.

At 416, the output of the signum function is added to the total of all previously calculated outputs and the count (C) is increased by 1. In doing so, over a given duration (j), which may start following an engine start and once the input parameters can be reliably sensed (e.g., yes to 310 as described with respect to FIG. 3) the routine determines for each sample instance (i) a classification CL based on the calibrated and trained support vector machine.

$$\left. \begin{array}{c} x1_i \\ x2_i \\ x3_i \\ x4_i \\ x5_i \end{array} \right\} \to SVM(x1_i, x2_i, x3_i, x4_i, x5_i) \to CL_i$$

Where CL is the output of the signum function, and is either set to 1 or −1, but with −1 converted to zero. Then, the routine adds $CL_i$ to the running count $C_j$:

$$C_j = C_{j-1} + C_j$$

The count (C) is compared to a first threshold at 418, and if C is above the threshold (e.g., the duration is complete) routine 400 proceeds to 422. If C is not above the threshold, routine 400 proceeds to 420 to continue to the next sample.

At 422, once the duration (j) is completed, the running count is divided by the total number of samples to determine a percentage of classifications where the catalyst was indicated to be functioning properly, or the percentage of the classifications with an output of 1 (% CL=1), and this percentage is compared to a second threshold. If the percentage is below a threshold percentage, then a degradation count (DC) is increased by 1 at 426. If the percentage is above the threshold percentage, then the degradation count DC may be reduced by 1 at 424. Both 424 and 426 proceed to 428 to determine if the total degradation count is greater than a third threshold. After a predetermined number of durations (e.g., j reaches ten, for example, indicating ten durations of samples have been completed), then if the degradation count is above a threshold, an indication may generated indicating the catalyst has degraded at 430. The indication may be sent to a driver via a message system, or may be the setting of a diagnostic code read by a diagnostic code reader in a service station, or various other indications such as a malfunction indicator lamp (MIL).

The duration (j) may any suitable duration. For example, in one embodiment, the duration may include a transient airflow condition where airflow is increasing greater than a threshold rate. This may include engine airflow that traverses a range from a minimum airflow corresponding to a closed throttle condition to a maximum airflow corresponding to a fully open throttle condition. In other embodiments, the duration may include catalyst temperature below a catalyst light-off temperature, a transient engine speed condition where engine speed is increasing greater than a threshold rate, etc. As stated above, more than one duration of samples may be collected during operation of the catalyst monitor. The plurality of durations may include combinations of the above durations. In some embodiments, the plurality of durations may occur successively, that is, without an engine shutdown occurring between them.

The indication of degradation is as determined by routine 400 may be based on the parameter readings occurring during the indicated duration. For example, the indication of degradation may be based on parameter readings occurring during the traversal of engine airflow from the minimum to the maximum airflows as explained above. Further, the indication of degradation may be based on parameter readings occurring while catalyst temperature is below light-off temperature, or may be based on parameter readings occurring when engine speed is increasing greater than a threshold rate.

It will be appreciated that the configurations and methods disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of monitoring catalyst performance, comprising:
    applying a set of parameter readings for a given sample to a support vector machine to generate a classification output;
    recording a plurality of classification outputs for a plurality of successive samples over a first duration; and
    indicating catalyst degradation if a threshold percentage of the classification outputs indicates degraded catalyst performance.

2. The method of claim 1, wherein the first duration includes a transient airflow condition where airflow is increasing greater than a threshold rate.

3. The method of claim 1, wherein the first duration includes catalyst temperature below a catalyst light-off temperature.

4. The method of claim 1, wherein the first duration includes a transient engine speed condition where engine speed is increasing greater than a threshold rate.

5. The method of claim 1, wherein the parameter readings include each of airmass, a linear exhaust air-fuel ratio upstream of the catalyst, and a binary exhaust air-fuel ratio downstream of the catalyst.

6. The method of claim 5, wherein the parameter readings include an estimate of a catalyst performance parameter indicative of the oxygen storage of the catalyst.

7. The method of claim 1, wherein the parameter readings include an estimated catalyst temperature.

8. The method of claim 1, wherein the support vector machine includes a non-linear transformation, and wherein clustering of data is performed to divide a data set into different clusters.

9. The method of claim 1, wherein the support vector machine includes a radial basis function kernel.

10. The method of claim 1, wherein engine airflow traverses a range from a minimum airflow corresponding to a closed throttle condition to a maximum airflow corresponding to a fully open throttle condition during the first duration, and where the indication of degradation is based on and includes the parameter readings occurring during the traversal of engine airflow from the minimum to the maximum airflows.

11. A method of monitoring catalyst performance, comprising:
    applying a set of parameter readings for a given sample to a support vector machine to generate a classification output;
    recording a plurality of classification outputs for a plurality of successive samples over a first duration;
    recording a plurality of classification outputs for a plurality of successive samples over a second duration following the first duration and without an engine shutdown occurring between the first and second durations; and
    indicating degradation of the catalyst if a percentage of the classification outputs is above a threshold level in each of the first and second durations.

12. The method of claim 11, wherein the first and/or second duration includes a transient airflow condition where airflow is increasing greater than a threshold rate.

13. The method of claim 11, wherein the first and/or second duration includes catalyst temperature below a catalyst light-off temperature.

14. The method of claim 11, wherein the first and/or second duration includes a transient engine speed condition where engine speed is increasing greater than a threshold rate, and wherein clustering of data is performed to divide a data set into different clusters.

15. The method of claim 11, wherein the parameter readings include each of airmass, a linear exhaust air-fuel ratio upstream of the catalyst, and a binary exhaust air-fuel ratio downstream of the catalyst.

16. The method of claim 15, wherein the parameter readings include an estimate of a catalyst performance parameter indicative of the oxygen storage of the catalyst and/or an estimated catalyst temperature.

17. The method of claim 11, wherein the support vector machine includes a non-linear transformation.

18. The method of claim 11, wherein the support vector machine includes a radial basis function kernel.

19. The method of claim 11, wherein engine airflow traverses a range from a minimum airflow corresponding to a closed throttle condition to a maximum airflow corresponding to a fully open throttle condition during the first and/or second duration, and where the indication of degradation is based on and includes the parameter readings occurring during the traversal of engine airflow from the minimum to the maximum airflows.

20. A method of monitoring catalyst performance, comprising:
    applying a set of parameter readings for a given sample to a support vector machine to generate a classification output;
    recording a plurality of classification outputs for a plurality of successive samples over a first duration;
    recording a plurality of classification outputs for a plurality of successive samples over a second duration following the first duration and without an engine shutdown occurring between the first and second durations; and
    indicating degradation of the catalyst if a percentage of the classification outputs for each of the first and second durations indicates the catalyst is degraded.

* * * * *